United States Patent [19]

Quante

[11] Patent Number: 4,847,194
[45] Date of Patent: Jul. 11, 1989

[54] COLORIMETRIC DETECTION OF DELTA-5-3-KETOSTEROID ISOMERASE AND IMMUNOASSAY BASED THEREON

[75] Inventor: J. Michael Quante, Durham, N.C.

[73] Assignee: Becton, Dickinson and Company, Franklin Lakes, N.J.

[21] Appl. No.: 25,710

[22] Filed: Mar. 13, 1987

[51] Int. Cl.$^4$ ...................... G01N 33/535; C12Q 1/00
[52] U.S. Cl. .......................................... 435/7; 435/4; 435/810
[58] Field of Search ............................... 435/7, 810, 4

[56] References Cited
U.S. PATENT DOCUMENTS

| 3,654,090 | 4/1972 | Hermans et al. | 435/7 |
| 4,298,686 | 11/1981 | Nicholas et al. | 436/808 |
| 4,350,760 | 9/1982 | Nicholas et al. | 435/7 |
| 4,769,321 | 9/1988 | Self | 435/21 |

OTHER PUBLICATIONS

Obuyama, Chemical Abstract, 87 (1977), abstract number 201867h.
Meyer et al, Anal. Chem., 27, 813–817, (1955).
Graham et al, J. Pharm. Science 64 (1975)·226–230.

Primary Examiner—Esther M. Kepplinger
Attorney, Agent, or Firm—Richard E. Brown

[57] ABSTRACT

A method for enzyme immunoassay includes contacting under binding conditions a liquid suspected of containing an analyte, an antianalyte and a tracer having conjugated thereto delta 5-3-ketosteroid isomerase. A bound fraction is separated from the liquid and incubated in a second liquid with a delta 5-3-ketosteroid substrate. Isomerase on the bound fraction converts the substrate to the corresponding delta 4-3-ketosteroid. A tetrazolium salt and a base are added. Unconverted delta 5-3-ketosteroid reduces the tetrazolium salt to a formazan which imparts a color to the liquid. A signal associated with the color may be used to detect or to measure the concentration of the analyte in the liquid. The invention includes a kit of materials useful in performing the assay of the invention.

22 Claims, 1 Drawing Sheet

⫘ ...... SOLID SUPPORT
Ab ..... ANTIBODY
Ag ..... ANTIGEN
E ...... ENZYME
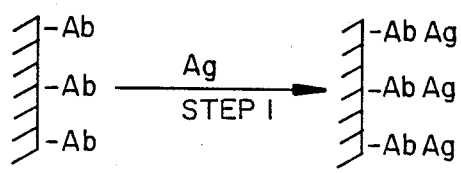
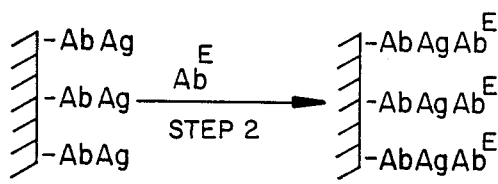
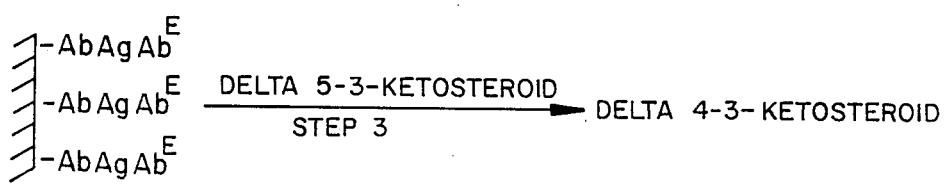
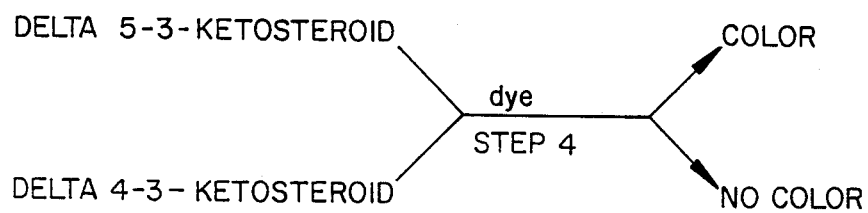

COLORIMETRIC DETECTION OF DELTA-5-3-KETOSTEROID ISOMERASE AND IMMUNOASSAY BASED THEREON

BACKGROUND OF THE INVENTION

1. Field of the Invention

This invention to immunoassay of an analyte and materials used therein, and more particularly relates to a method and materials for enzyme immunoassay using delta 5-3-ketosteroid isomerase.

2. Background of the Invention

A variety of assay systems which are both rapid and sensitive has been developed to detect or determine the concentration of a substance, generally referred to as the analyte, in a liquid. Immunoassays depend on the binding of the analyte to a specific antianalyte, and have been particularly useful because they give high levels of specificity and sensitivity. These assays generally employ one of the above reagents in labeled form, the labeled reagent often being referred to as the tracer. Immunoassay procedures may be carried out in solution or on a solid support, and are of two basic types. In competitive assays, the tracer is labeled analyte, and the analyte and tracer compete for a limited number of antianalyte binding sites. In sandwich assays, the tracer is a labeled second antianalyte specific for a second determinant on the analyte giving an antianalyte-analyte-labeled antianalyte sandwich.

Various means for labeling have been developed. Radioimmunoassay (RIA) procedures use radioisotopes as labels, provide high levels of sensitivity and reproducibility, and are amenable to automation for rapid processing of large numbers of samples. However, all RIA procedures require a separation step, since the parameter measured (nuclear decay) cannot be controlled by changing assay conditions or components. In addition, isotopes are costly, have relatively short shelf lives, require expensive and complex equipment, and extensive safety measures for their handling and disposal must be followed.

Fluoroimmunoassay (FIA) uses fluorochromes as labels, provides direct detection of the label, and is readily adaptable to homogeneous assay procedures. However, known homogeneous FIA methods using organic fluorochromes, such as fluorescein or rhodamine derivatives, have not achieved the high sensitivity of RIA, largely because o light scattering by impurities suspended in the assay medium and by background fluorescence emission from other fluorescent materials present in the assay medium.

Enzymes have also been used as labels in immunoassay. Enzyme immunoassay (EIA) combines the advantages of RIA and FIA and overcomes many of the disadvantages of the other two methods. Enzyme labeled reagents are cheap to prepare and are highly stable thus giving a long shelf life, yet yield assays which approach the sensitivity of radioimmunoassay and which give objective results that can be determined, either visually, or with rather simple equipment, such as a spectrophotometer.

In conventional EIA, an enzyme is covalently conjugated with one component of a specifically binding antigen-antibody pair, and the resulting enzyme conjugate is reacted with a substrate to produce a color wich is measured. Often, an unconjugated component is immobilized on a solid support. Representative of such conventional EIA is U.S. Pat. No. 3,654,090 to Schuurs et al.

Many enzymes, such as horseradish peroxidase and alkaline phosphatase have been used as labels in EIA. U.S. Pat. No. 4,298,686 discloses use of delta 5-3-ketosteroid isomerase conjugated to an antigen as a label in a method for EIA in which ultraviolet spectroscopy is used to detect the label.

Redox reactions between delta 4-3-ketosteroids and tetrazolium salts are conventionally used in analysis of corticosteroids (the "blue tetrazolium reaction"). Discussions of this procedure are given by Meyer et al. in Anal. Chem. 27, 813 (1955) and by Graham et al. in J. Pharm. Sci. 64, 226 (1975).

An EIA method including colorimetric detection of delta 5-3-ketosteroid isomerase which would provide rapid visual detection of highly dilute analytes and avoid the need for expensive instrumentation would be desirable. The present invention is directed toward this objective.

SUMMARY OF THE INVENTION

An antianalyte specific for an analyte is contacted with a liquid suspected of containing the analyte and a tracer labeled with delta 5-3-ketosteroid isomerase, (hereinafter referred to as rhe enzyme). After binding reactions involving the antianalyte, analyte and enzyme-labeled tracer, the liquid is separated and the bound phase in a second liquid is contacted with a substrate for the enzyme, a tetrazolium salt and a base. Enzyme associated with the bound phase reacts with the substrate. Unchanged substrate reduces the tetrazolium salt to a formazan whereby color develops in the second liquid. A signal associated with the color is proportional to the quantity of enzyme bound by the antianalyte.

In one embodiment of the invention, the tracer may be the analyte conjugated to the enzyme, and the assay may be performed by a competitive technique using a limited quantity of antianalyte so that the quantity of enzyme bound is inversely proportional to the concentration of the analyte in the liquid. In a preferred embodiment of the invention, a sandwich assay technique using sufficient antianalyte affixed to a solid support to bind substantially all of the analyte may be used. In this preferred embodiment, the tracer may be a second antianalyte having the enzyme conjugated thereto so that the quantity of bound enzyme is directly proportional to the analyte concentration.

In a preferred embodiment of the invention, the substrate is a $\beta$, $\gamma$-unsaturated ketosteroid and the base is a tertiary amine.

In the most preferred embodiment of the invention, an antigen in a body fluid may be detected by a sandwich assay using a specific antibody affixed to a solid support to bind the antigen and a tracer comprising an enzyme-labeled second specific antibody. The bound phase may be separated from the fluid and added to a second liquid. A delta 5-3-ketosteroid substrate is added, and the liquid may incubated to allow the enzyme to react with the substrate. Blue tetrazolium chloride and a tertiary amine are added, any unchanged delta 5-3-ketosteroid reducing the blue tetrazolium chloride to a formazan which imparts color to the liquid. The color may be measured after a specified time wherein the presence of antigen in the fluid is indicated by inhibition of color formation.

The method may be adapted to determine the concentration of the antigen in the fluid by comparing color intensity of the unknown with the color generated when a liquid containing a predetermined quantity of the antigen is assayed under substantially the same conditions.

Thus, a hitherto unknown combination of reactions between the enzyme, a delta 5-3-ketosteroid and a tetrazolium salt has been discovered which is applicable to a method for EIA. In the conventional "blue tetrazolium reaction," delta 4-3-ketosteroids react with the dye to give a color. in contrast, the method of this invention depends on the discovery of conditions under which delta 5-3-ketosteroids react with the tetrazolium salt while delta 4-3-ketosteroids do not. Color formation is proport the extent of the enzymatic reaction and thereby provides a visual detection of the enzyme ueeful in an EIA. Since no instrumentation is required, the method of the invention provides advantages and improvements over existing methods.

BRIEF DESCRIPTION OF THE DRAWINGS

The FIGURE is a flow sheet showing the sequence of steps in the preferred assay of the invention.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the method of the invention, a substance, hereinafter referred to as the analyte, suspected of being present in a liquid, may be detected visually, i.e., by naked eye observation, even when present in very low concentrations. Detection is accomplished by a colorimetric method based on conversion of a delta 5-3-ketosteroid substrate to a delta 4-3-ketosteroid product by the enzyme. Under suitable assay conditions, the delta 5-3-ketosteroid substrate reduces a tetrazolium dye to a colored formazan whereas the corresponding delta 4-3-ketosteroid does not reduce the dye and thus does not cause color to develop.

The method of the present invention includes an immunological reaction. By the term "immunological reaction," as used herein, is meant a specific binding reaction of an antigen and an antibody, a hapten and an antibody, or any appropriate analogue of an antigen, an antibody, or a hapten which also binds specifically. The immunological reaction may be carried out in any suitable liquid. For example, the liquid may be a body fluid suspected of containing the analyte, such as serum urine, cerebrospinal fluid, pleural fluid or the like. Alternatively, the liquid may be water, saline or any appropriate buffer, or a mixture of body fluids and other liquids to which has been added a sample suspected of containing ligand.

It is preferred, but not essential, that one or more of the assay components be attached to the surface of a solid support. As known in the art, the solid support may be any support which does not substantially interfere with the assay. Exemplary of solid supports which may be used are glass and polymeric materials, such as polyethylene, polystyrene and the like. Such supports may be fabricated into any suitable shape, such as sheets, tubes, wells, or preferably, plates such as microtiter plates. For example, an assay component, preferably the antianalyte (described below), may be attached to the inside walls and bottom of a tube, preferably a plastic tube with one closed end, or most preferably, to the wells of a microtiter plate.

Subsequent to attachment of the assay components to the solid support, any remaining binding sites on the support may preferably be filled with an inert protein, such as, for example, albumin. Attachment of an assay component or an inert protein to a solid support is generally carried out by absorption or covalent conjugation. Such procedures are conventional and well known to those skilled in the art.

Either a competitive or a sandwich assay may be used in the method of the invention. The preferred sandwich assay will first be described with reference to the assay flow sheet depicted FIGURE to provide a general understanding of the assay components and their interaction, after which each component will be discussed in detail.

It is seen from FIGURE that a solid support having affixed thereto an antibody specific for an antigen is contacted with a liquid suspected of containing the antigen, and conditions conducive to binding the antigen to the antibody are provided (Step 1). A second antibody (labeled $A^E_b$ in the drawing), specific for a different determinant of the antigen and having enzyme conjugated thereto, is contacted under binding conditions to provide an antibody-antigen-antibody sandwich on the support (Ste 2). After a conventional separation of the support from the liquid, the sandwich on the support is contacted with a delta 5-3-ketosteroid substrate (Step 3). The enzyme component of the second antibody on support converts the substrate to a delta 4-3-ketosteroid, the extent of the conversion being proportional to the quantity of bound enzyme, which in turn is proportional to the quantity of antigen in the liquid. In Step 4, a tetrazolium salt is added. Any remaining delta 5 substrate reacts with the dye to give a color, but the delta 4-3-ketosteroid formed by the enzymatic reaction does not react with the dye and thus does not cause color formation. The color formed, or its rate of formation, may be measured to indicate the presence of antigen in the liquid.

Turning now to a detailed description of the assay components, the analyte may be from any source, and may be an antigen, an antibody or a hapten. For example, the analyte may be an antigen present in a body fluid, or it may be isolated from a body fluid and subsequently introduced into a different liquid, such as buffer. In other cases, the analyte may be from a source other than a body fluid, as, for example, a culture of microorganisms or a cellular extract thereof. Preferred analytes are antigens, most preferably viral antigens present in a body fluid, such as Herpes simplex virus (HSV), Adenovirus, Influenza A virus, Parainfluenza 3 virus and Respiratory syncytial virus.

The antianalyte may be an antigen or an antibody, either monoclonal or poplyclonal, or it may be any appropriate analogue thereof which reacts specifically with the analyte. The preferred antianalyte is an antibody specific for an antigen analyte. The antianalyte may also be an antibody complex consisting of a plurality of bound antibodies, as, for example, a second antibody bound specifically to a first antibody, or it may be an ensemble of polyclonal antibodies or a mixture of several monoclonal antibody molecules which bind simultaneously to different surface areas of the analyte. Generally, the second antibody is raised against the first antibody in a different species. The plurality of bound antibodies in the complex may contain from about two to ten or more antibodies.

With respect to the quantity of antianalyte, it is preferred in a sandwich assay to use excess antianalyte so that sufficient binding sites are available to bind essentially all of the analyte. As will be described later, a limited quantity of antianalyte is preferred in a competitive assay.

The tracer comprises two components, the enzyme conjugated to analyte or to a second antianalyte. The enzyme may be conjugated to the analyte or antianalyte in any suitable way, preferably by a covalent linkage, prior to the immunological reaction. Covalent conjugation of enzymes to ligands such as antigens or antibodies is conventional and well known to those skilled in the art.

The assay medium containing the analyte, the antianalyte and the tracer may be incubated, if necessary, to induce binding. Incubation may be carried out at any temperature and for any length of time suitable to facilitate binding, preferably from about 20° C. to 40° C. for about one minute to four hours. Antianalyte, analyte and tracer which are bound are hereinafter referred to as the bound fraction and antianalyte, analyte and tracer which do not bind are hereinafter referred to as the free fraction. The assay may, but need not, be carried out in such a way that equilibrium is established between the bound and free fractions.

Any conventional method, such as filtration, decantation, centrifugation, aspiration and the like, may be used to separate the bound fraction from the free fraction in the liquid phase of the assay mixture. When the immunological reaction has been carried out on a solid support, the liquid phase is conveniently decanted, the solid support washed to ensure removal of the free fraction and any other materials which would interfere with the assay, resuspended in a suitable second liquid such as water, saline, buffer, alcohols, polar aprotic solvents or mixtures thereof, and a substrate for the enzyme added.

The substrate may be a reagent which reacts with the dye to give a color and which reacts with the enzyme to give a product which does not react with the dye. (The term product is herein used to mean the substance formed from the substrate by the enzyme.) Suitable substrates are all delta 5-3-ketosteroids, including delta 5(6)- and delta 5(10)-3-ketosteroids. Preferred substrates are delta 5-pregnene-3,20-dione, delta 5(6)-estrene-3,17-dione, delta 5(10)-estrene-3,17-dione, delta 5(10)-estrene-17-alpha ethynyl-17-beta hydroxy-3-one and, most preferably delta 5-androstene-3,17-dione.

The solid phase having enzyme thereon may preferably be incubated with the substrate in the second liquid to ensure conversion of the substrate to the product prior to addition of the dye. Suitable dyes are tetrazolium salts which react in the presence of an appropriate base with the substrate to produce colored formazans, but which do not react under substantially the same conditions with the product. The preferred dye is tetrazolium blue chloride which undergoes a redox reaction in the presence of the base with a delta 5-3-ketosteroid to give a red formazan but which does no react with a delta 4-3-ketosteroid under substantially the same conditions.

Any base may be used which promotes the redox reaction between the substrate and the dye without promoting any substantial reaction between the product and the dye or, independent of enzyme, causing any substantial conversion of substrate to product. The base promotes a reaction between the $\beta$, $\gamma$-unsaturated ketosteroid and the tetrazolium salt without promoting any substantial reaction between an $\alpha$,$\beta$-unsaturated ketosteroid and the tetrazolium salt and without causing any substantial isomerization of said $\beta$,$\gamma$-unsaturated ketosteroid to said $\alpha$,$\beta$-unsatuated ketosteroid. For example, suitable bases do not substantially catalyze the isomerization of delta 5-3-ketosteroid to delta 4-3-ketosteroids or promote reaction of the dye with delta 4-3-ketosteroids. Preferred bases are tertiary amines, such as, for example, triethylamine, diisopropylethylamine, N-methylpiperidine and the like.

The dye and base may preferably be dissolved in a solvent prior to combining with the second liquid. Suitable solvents are miscible with water and do not in any way interfere with the assay components or reactions. Preferred solvents are polar aprotic solvents such as dimethylformamide and dimethylsulfoxide, alcohols, water or mixtures thereof. The quantities of the assay components to be used, and their concentrations in the assay liquids, are well within the purview of those skilled in the art, and no further details in this respect are needed for a complete understanding of the invention.

If desired, the bound phase having enzyme thereon may be brought into contact with the substrates, dye and base substantially simultaneously; however, it is preferred to cause reaction of the enzyme and substrate separately prior to addition of dye and base, as described above.

Reaction of the dye with substrate not converted to product by the enzyme causes color to develop in the assay liquid. A signal associated with the color may be used to detect or measure the analyte. For example, the signal may be the intensity of the color which develops, or it may be the inhibition of color to development.

Measurements of the signal may be made under either kinetic or thermodynamic conditions. Kinetic measurements determine the rate of color development which occurs over a period of time, and are generally carried out by making a series of measurements at various times after combining the assay reagents. Thermodynamic measurements determine the extent of color formation which has occurred after a specified time. Measurements may be made either instrumentally, as for example, with a colorimeter, or preferably, with the naked eye.

In the preferred solid phase sandwich assay of the invention, the quantity of enzyme bound to the solid phase is directly proportional to the quantity of antigen in the liquid. Since the color to be measured is formed by reaction of the enzyme substrate with the dye, it is seen that color intensity is directly proportional to substrate concentration, and thus inversely proportional to enzyme (and thus antigen) level. Lack of color thus indicates antigen in the liquid.

As mentioned earlier, another embodiment of the invention is a competitive assay wherein the tracer is the analyte conjugated to the enzyme. In a competitive assay, insufficient antianalyte is used to bind all of the analyte and tracer present in the assay liquid so that analyte and tracer compete for the limited number of antianalyte binding sites. Thus, the quantities of analyte and tracer which bind to the antianalyte (bound fraction) are directly proportional to their concentrations in the assay liquid. Accordingly, when the method of the invention is carried out by the competitive technique, a high concentration of antigen will cause a low concentration of enzyme on the bound phase. When the level of bound enzyme is low, most of the substrate remains unchanged and therefore reacts with the dye to generate intense color. Conversely, low antigen concentration will lead sequentially to high enzyme level on the bound phase, high conversion of substrate to product so that little substrate remains unchanged to react with dye, and finally therefore o little color.

It is evident that an almost unlimited number of competitive and sandwich assay configurations which fall within the scope of the invention are envisioned. Further, the invention provides assay configurations which are suitable for either detection of the analyte or determination of analyte concentration. Analyte concentration may be determined by comparing the magnitude of the signal generated with the unknown sample with the magnitude of the signal measured upon assay of a range of known quantities of the analyte assayed under essentially identical conditions. When the method of the invention is to be used for determination of analyte concentration, color intensity from the analyte may be compared visually with a series of standards, or preferably color intensity may be determined and compared with standards using an appropriate instrument, such as a colorimeter or a spectrophotometer.

Another aspect of the invention is a reagent kit or package of materials for performing an assay for an analyte in accordance with the method of the invention. The kit may include an antianalyte, optionally affixed to a solid support, a tracer comprising delta 5-3-ketosteroid isomerase conjugated to the analyte or a second antianlyte, and a tetrazolium salt. The kit may also include standards for the analyte, as, for example, one or more analyte samples of known concentration, or it may include other reagents, such as a base or an enzyme substrate. It may include solutions, such as saline, buffers, alcohols or polar aprotic solvents useful in carrying out the assay. The components of the kit may be supplied in separate containers, as, for example, vials, or two or more of the components may be combined in a single container.

EXAMPLE I

Two ml of saturated ethanolic blue tetrazolium chloride and five drops of the base indicated in Table I below were added to each of 20 tubes. The tubes were divided into four groups of five tubes each and ethanolic solutions of the steroids listed in the table were added to the tubes to provide one tube containing each steroid-base combination. The tubes were observed for color development after five minutes. The results are given in Table I:

TABLE I

| STEROID | BASE 1 | BASE 2 | BASE 3 | BASE 4 | BASE 5 |
|---|---|---|---|---|---|
| delta 4-estrene-3,17-dione | +violet | +red | +red | — | — |
| delta 4-androstene-3,17-dione | +red | +red | +red | — | — |
| hydrocortisone | ++ blue ppt | ++ violet ppt | + violet ppt | — | + light pink |
| delta 5-androstene-3,17-dione | +red | +red | +red | — | +red |

TABLE I-continued

| STEROID | BASE 1 | BASE 2 | BASE 3 | BASE 4 | BASE 5 |
|---|---|---|---|---|---|

KEY TO TABLE:
BASE 1—benzyltrimethylammonium hydroxide
BASE 2—tetrabutylammonium hydroxide
BASE 3—choline hydroxide
BASE 4—triethanolammonium hydroxide
BASE 5—triethylamine
++—very strong, instantaneous color formation
+—strong, rapid color formation
——extremely weak or no color formation It is seen that, with triethylamine as the base, the delta 5-dione gave a strong positive color but the delta 4-diones did not. Hydrocortisone, though a delta 4-steroid, gave a pink color. It is postulated that this color results from the reaction of an α-ketol intermediate of this compound, consistent with the blue tetrazolium reaction used in the aforementioned conventional analysis of corticosteroids.

EXAMPLE 2

Solutions of two drops of the following tertiary amines in 0.5 ml of saturated ethanolic tetrazolium blue chloride were mixed with 0.5 ml of $1.5 \times 10^{-3}$M ethanolic solutions of delta 4- and delta 5-androstene-3,17-dione and observed for color formation.

The results are given in Table II:

TABLE II

| STEROID | BASE 5 | BASE 6 | BASE 7 | BASE 8 | BASE 9 |
|---|---|---|---|---|---|
| delta 5-androstene-3,17-dione | + | ++ | + | ++ | + |
| delta 4-androstene-3,17-dione | — | — | — | + | — |

BASE 5—triethylamine
BASE 6—diisopropylethylamine
BASE 7—N,N,N',N'—tetramethylethylenediamine
BASE 8—1,8-diazabicyclo [5,4,0] undec-7-ene
BASE 9—1,4-dioxa-8-azaspiro [4.5] decane The positive result with the delta 4-steroid in the presence of BASE 8 is believed to be due to BASE 8 itself.

EXAMPLE III

Two sets of five tubes each were charged at time zero with 800 ul of $3.5 \times 10^{-3}$M delta 5-androstene-3, 17-dione in ethanol. The tubes of the first set received 200 ul of $6.2 \times 10^{-9}$M solution of enzyme in water (test). The tubes of the second set received water only (control). At times 0,5,10,20 and 30 minutes, a 60 ul aliquot from each tube was added to 940 ul of a stock saturated ethanolic solution of tetrazolium blue chloride containing four drops of triethylamine. Test and control tubes for each time were compared. The results are given in Table III.

TABLE III

| | Time (minutes) | | | | |
|---|---|---|---|---|---|
| | 0 | 5 | 10 | 20 | 30 |
| Set 1 (test) | ++ | + | + | (−) | — |
| Set 2 (control) | ++ | ++ | ++ | ++ | ++ |

KEY
++—dark red
+—red
(−)—light pink
——colorless

It is seen that the enzyme in the tubes of the test set converted the delta 5-substrate to product over the time span of the experiment, and that, as product increased and substrate decreased, color formation decreased.

EXAMPLE IV

The wells of a microtiter plate were divided into three groups. Group I wells received 100 ul of a 10 ug/ml solution of the gβ antigen from HSV-1 virus. Group II and III wells received a solution of carbonate coating buffer (0.045 M sodium bicarbonate, 0.018 M sodium carbonate and 0.02 M of ethylenediamine-tetraacetic acid at pH 9.4–9.6. All wells were washed with casein buffer prepared from 154 mM NaCl, 0.5% casein and 10 mM tris(hydroxymethyl)aminomethane (TRIZ-MA$^R$) adjusted to pH 7.6. The wells of Group I and II were incubated for one hour at 37° C. with 100 ul of a stock solution of anti HSV-1 antibody conjugated to a quantity of delta 5-3-ketosteroid isomerase in casein buffer containing 5% gelatin and 10% fetal calf serum capable of converting 20 umole delta 5-androstene-3,17-dione to delta 4-androstene-3, 17-dione per minute per milliliter. Excess conjugate solution was decanted and all wells were washed three times with buffer composed of 154 mM NaCl and 10 mM Trizma$^R$ at pH 8. Fifty ul of a $3.95 \times 10^{-3}$ M solution of delta 5-3-ketosteroid substrate in 1:1 dimethylformamide-H$_2$O were added to each well. After the plaee had been incubated for two hours at 25° C., 150 ul of a $2.14 \times 10^{-2}$ M saturated solution of tetrazolium blue chloride in ethanol containing 10% by volume diisopropylethylamine were added to each well. After ten minutes, the colors of the wells were visually examined and the optical densities were determined at 510 nm with a Titertek Multiskan MC (Type 340, Flow Laboratories). The results are given in Table IV.

TABLE IV

|  | Group I | Group II | Group III |
|---|---|---|---|
| color | pink | dark red | dark red |
| optical density | 1.23 | 2.65 | 2.70 |

It is seen that the antigen-containing wells of Group I bound the antibody conjugate and thereby captured enzyme, whereas the antibody added to the Group II wells was washed away. Thus, only the Group I wells retained enzyme. Substrate concentration in the Group I wells was reduced because the retained enzyme isomerized the substrate to product, and as a consequence, color did not develop strongly in these wells because product (delta 4-3-ketosteroid) does not reduce the dye. On the other hand, absence of enzyme in the Group II and III wells left the substrate in these wells unchanged and available to reduce the dye and cause formation of intense color.

In summary, conditions have been found under which delta 5-3-ketosteroids, but not delta 4-3-ketosteroids, react with a tetrazolium dye to give a colored formazan. This selective reaction is utilized in an immunoassay for an analyte which depends on the enzymatic conversion of delta 5-3-ketosteroids to delta 4-3-ketosteroids by the nzyme delta 5-3-ketosteroid isomerase. A visual ignal based on the color of the assay medium due to ormazan formation is used to detect the analyte.

What is claimed is:

1. A method for detecting an analyte in a liquid comprising:

(a) contacting a solid support having affixed thereto an antianalyte specific for an analyte with a first liquid suspected of containing said analyte and with a tracer which includes delta 5-3-ketosteroid isomerase whereby said analyte binds to said antianalyte and said tracer binds to one of said analyte and said antianalyte to give a bound fraction on said support;

(b) separating said support from said first liquid;

(c) contacting said support in a second liquid with a β,γ-unsaturated ketosteroid, a solution of a salt of tetrazolium blue and a base in a solvent, said base promoting a reaction between said β,γ-unsaturated ketosteroid and said tetrazolium blue without promoting any substantial reaction between an α,β-unsaturated ketosteroid and said tetrazolium blue and without causing any substantial isomerization of said β,γ-unsaturated ketosteroid to said α,β-unsaturated ketosteroid, whereby said tetrazolium blue is reduced to a formazan, said formazan imparting color to said second liquid; and (d) detecting said analyte by a signal associated with said color.

2. The method in accordance with claim 1 wherein said tracer binds to said antianalyte and further comprises sid analyte having said delta 5-3-ketosteroid isomerase conjugated thereto.

3. The method in accordance with claim 1 wherein said tracer binds to said analyte and further comprises a second antianalyte having said delta 5-3-ketosteroid isomerase conjugated thereto.

4. The method in accordance with claim 1 wherein said solid support further comprises an inert protein which fills binding sites of the support unoccupied by antianalyte.

5. The method in accordance with claim 1 wherein said analyte is selected from the group consisting of an antigen, an antibody and a hapten.

6. The method in accordance with claim 1 wherein said antianalyte is selected from the group consisting of an antigen, an antibody and an antibody complex.

7. The method in accordance with claim 1 wherein said β,γ-unsaturated ketosteroid is a delta 5-3-ketosteroid.

8. The method in accordance with claim 1 wherein said base is a tertiary amine.

9. The method in accordance with claim 8 wherein said tertiary amine is selected from the group consisting of triethylamine, diisopropylethylamine, N-methylpiperidine, N,N,N',N'-tetramethylethylenediamine, 1,8-diazabicyclo [5.4.0] undec-7-ene and 1,4-dioxa-8-azaspiro [4.5] decane.

10. The method in accordance with claim 1 wherein said second liquid is selected from the group consisting of water, saline, an alcohol and a polar aprotic solvent.

11. The method in accordance with claim 1 wherein said solvent is selected from the group consisting of water, alcohol and a polar aprotic solvent.

12. The method in accordance with claim 1 further comprising incubating said second liquid subsequent to said contacting with β,γ-unsaturated ketosteroid and prior to said contacting with said solution.

13. A method for detecting an analyte in a liquid comprising:

(a) contacting an antianalyte specific for an analyte with a first liquid suspected of containing said analyte and with a tracer which includes delta 5-3-ketosteroid isomerase whereby said analyte binds to said antianalyte and said tracer binds to one of said analyte and said antianalyte to give a bound fraction;

(b) separating said bound fraction from said first liquid;

(c) contacting said bound fraction in a second liquid with a substrate for said enzyme, a base and a tetrazolium salt capable of being reduced to a formazan by said substrate, said base promoting a reaction between said substrate and said tetrazolium salt said formazan imparting color to said second liquid; and (d) detecting said analyte by a signal associated with said color.

14. A method for detecting an antigen in a liquid comprising:

(a) contacting a solid support having affixed thereto a first antibody with a first liquid suspected of containing an antigen and with a second antibody conjugated to delta 5-3-ketosteroid isomerase whereby said first and second antibodies bind to said antigen to give a bound fraction on said support;

(b) separating said support from said first liquid;

(c) incubating said support in a second liquid with a delta 5-3-ketosteroid whereby said isomerase isomerizes said delta 5-3-ketosteroid to a delta 4-3-ketosteroid;

(d) adding to said second liquid a solution of a tertiary amine and blue tetrazolium chloride in a solvent whereby there is formed a formazan which imparts a color to said liquid; and (e) detecting said antigen by a signal associated with said color.

15. A method for determining an analyte in a liquid comprising:

(a) contacting an antianalyte specific for an analyte with a first liquid suspected of containing said analyte and with a tracer which includes delta 5-3-ketosteroid isomerase whereby said analyte binds to said antianalyte and said tracer binds to one of said analyte and said antianalyte to give a bound fraction;

(b) separating said bound fraction from said first liquid;

(c) contacting said bound fraction in a second liquid with a delta 5-3-ketosteroid, a salt of tetrazolium blue and a base, said base promoting a reaction between said delta 5-3-ketosteroid and said tetrazolium blue promoting any substantial reaction between delta 4-3-ketosteroid and said tetrazolium blue and without causing any substantial isomerization of said delta 5-3-ketosteroid to said delta 4-3-ketosteroid, whereby said tetrazolium blue is reduced to a formazan, said formazan imparting color to said second liquid;

(d) measuring the color of said second liquid; and (e) comparing the color of said second liquid with the color of a liquid containing a predetermined quantity of said analyte treated substantially in accordance with steps (a) to (d).

16. A kit of materials for performing an assay for an analyte comprising an antianalyte specific for said analyte, a tracer which includes delta 5-3-ketosteroid isomerase and a tetrazolium salt.

17. The kit in accordance with claim 16 wherein said antianalyte is attached to a solid support.

18. The kit in accordance with claim 16 furhter comprising at least one other reagent selected from the group consisting of an enzyme substrate for said isomerase, base, buffer, saline, alcohol and polar aprotic solvent said base promoting a reaction between said substrate and said tetrazolium salt.

19. The kit in accordance with claim 18 wherein said substrate is a delta 5-3-ketosteroid.

20. The kit in accordance with claim 16 further comprising at least one liquid containing analyte of known concentration.

21. The kit in accordance with claim 16 further comprising a liquid substantially free of analyte.

22. The kit in accordance with claim 16 further comprising one or more containers.

* * * * *